US010182973B2

United States Patent
Steckel et al.

(10) Patent No.: US 10,182,973 B2
(45) Date of Patent: Jan. 22, 2019

(54) POLYMERIC BONE FOAM COMPOSITION AND METHOD

(75) Inventors: Hartwig Steckel, Kiel (DE); Maren Kuhli, Pfaffenhofen (DE); Torben Christian Sörensen, Mönkeberg (DE); Nils Reimers, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 1354 days.

(21) Appl. No.: 13/884,423

(22) PCT Filed: Nov. 10, 2010

(86) PCT No.: PCT/EP2010/067196
§ 371 (c)(1),
(2), (4) Date: Jul. 16, 2013

(87) PCT Pub. No.: WO2012/062360
PCT Pub. Date: May 18, 2012

(65) Prior Publication Data
US 2014/0012271 A1    Jan. 9, 2014

(51) Int. Cl.
*A61L 24/02* (2006.01)
*A61K 6/00* (2006.01)
(Continued)

(52) U.S. Cl.
CPC ........ *A61K 6/0047* (2013.01); *A61B 17/8805* (2013.01); *A61K 47/02* (2013.01);
(Continued)

(58) Field of Classification Search
CPC ............. A61B 17/8805; B01F 3/04446; B01F 13/0023; B01F 15/0087; A61K 47/02;
(Continued)

(56) References Cited

U.S. PATENT DOCUMENTS 2,018,410 A    10/1935  McDonald
3,318,774 A     5/1967  Dingwall et al.
(Continued)

FOREIGN PATENT DOCUMENTS

AU    2006201475 A1    10/2006
CA       2540927 A1    10/2006
(Continued)

OTHER PUBLICATIONS

Abstract of: Desai et al. Drug Deliv. 2006, 13(1), 39-50) 1 page.
(Continued)

*Primary Examiner* — Anu Ramana
(74) *Attorney, Agent, or Firm* — Lerner, David, Littenberg, Krumholz & Mentlik, LLP

(57) ABSTRACT

Biomaterials, in particular bone foams, a process for preparing such materials as well as an applicator for applying the biomaterials directly to the patient's application site, and the use of a composition comprising water, a surfactant and a propellant in the preparation of a bone foam for the preparation of a calcium phosphate foam wherein the foam is obtainable by the mixture of at least two phases, a first phase comprising water and optionally a propellant, a second phase comprising one or more sources for calcium and/or phosphate, and wherein the foaming is performed during the mixture of the at least two phases to provide an improved calcium phosphate foam, process for the preparation of a calcium phosphate foam, use of a composition, solid state structure, calcium phosphate cement foam and bone foam applicator.

10 Claims, 1 Drawing Sheet

(51) Int. Cl.

| | | |
|---|---|---|
| *A61B 17/88* | (2006.01) | |
| *B01F 3/04* | (2006.01) | |
| *B01F 13/00* | (2006.01) | |
| *B01F 15/00* | (2006.01) | |
| *C04B 26/16* | (2006.01) | |
| *C04B 38/10* | (2006.01) | |
| *A61K 47/02* | (2006.01) | |

(52) U.S. Cl.
CPC ...... *B01F 3/04446* (2013.01); *B01F 13/0023* (2013.01); *B01F 15/0087* (2013.01); *C04B 26/16* (2013.01); *C04B 38/103* (2013.01)

(58) Field of Classification Search
CPC .......... A61K 9/12; A61K 9/122; A61K 9/124; C04B 38/103; C04B 14/366; C04B 22/002
See application file for complete search history.

(56) References Cited

U.S. PATENT DOCUMENTS

| | | |
|---|---|---|
| 3,968,567 A | 7/1976 | Nevins |
| 4,139,599 A | 2/1979 | Tomlinson et al. |
| 4,244,931 A | 1/1981 | Jarvis et al. |
| 4,312,843 A | 1/1982 | Monty et al. |
| 4,472,365 A | 9/1984 | Michel |
| 4,612,053 A | 9/1986 | Brown et al. |
| 4,772,468 A | 9/1988 | Pfirrmann |
| 4,828,823 A | 5/1989 | Li |
| 4,843,112 A | 6/1989 | Gerhart et al. |
| 4,861,733 A | 8/1989 | White |
| 4,869,906 A | 9/1989 | Dingeldein et al. |
| 4,880,610 A | 11/1989 | Constantz |
| RE33,161 E | 2/1990 | Brown et al. |
| RE33,221 E | 5/1990 | Brown et al. |
| 4,973,168 A | 11/1990 | Chan |
| 5,024,825 A | 6/1991 | Buhl et al. |
| 5,047,031 A | 9/1991 | Constantz |
| 5,053,212 A | 10/1991 | Constantz et al. |
| 5,129,905 A | 7/1992 | Constantz |
| 5,137,534 A | 8/1992 | Sumita |
| 5,149,368 A | 9/1992 | Liu et al. |
| 5,162,430 A | 11/1992 | Rhee et al. |
| 5,178,845 A | 1/1993 | Constantz et al. |
| 5,262,166 A | 11/1993 | Liu et al. |
| 5,336,264 A | 8/1994 | Constanz et al. |
| 5,342,441 A | 8/1994 | Mandai et al. |
| 5,398,483 A | 3/1995 | Smith et al. |
| 5,427,756 A | 6/1995 | Dany et al. |
| 5,434,440 A | 7/1995 | Yoshitomi et al. |
| 5,522,893 A | 6/1996 | Chow et al. |
| 5,525,148 A | 6/1996 | Chow et al. |
| 5,542,973 A | 8/1996 | Chow et al. |
| 5,545,254 A | 8/1996 | Chow et al. |
| 5,569,442 A | 10/1996 | Fulmer et al. |
| 5,605,713 A | 2/1997 | Boltong |
| 5,683,496 A | 11/1997 | Ison et al. |
| 5,697,981 A | 12/1997 | Ison et al. |
| 5,709,742 A | 1/1998 | Fulmer et al. |
| 5,782,971 A | 7/1998 | Constantz et al. |
| 5,797,873 A | 8/1998 | Franz et al. |
| 5,820,632 A | 10/1998 | Constantz et al. |
| 5,846,312 A | 12/1998 | Ison et al. |
| 5,900,254 A | 5/1999 | Constantz |
| 5,952,010 A | 9/1999 | Constantz |
| 5,954,867 A | 9/1999 | Chow et al. |
| 5,962,028 A | 10/1999 | Constantz |
| 5,968,253 A | 10/1999 | Poser et al. |
| 5,968,999 A | 10/1999 | Ramp et al. |
| 6,002,065 A | 12/1999 | Constantz et al. |
| 6,005,162 A | 12/1999 | Constantz |
| 6,030,635 A | 2/2000 | Gertzman et al. |
| 6,117,456 A | 9/2000 | Lee et al. |
| 6,117,979 A | 9/2000 | Hendriks et al. |
| 6,201,039 B1 | 3/2001 | Brown et al. |
| 6,206,957 B1 | 3/2001 | Driessens et al. |
| 6,235,665 B1 | 5/2001 | Pickrell et al. |
| 6,277,151 B1 | 8/2001 | Lee et al. |
| 6,318,841 B1 | 11/2001 | Coleman et al. |
| 6,340,648 B1 | 1/2002 | Imura et al. |
| 6,375,935 B1 | 4/2002 | Constantz |
| 6,379,453 B1 | 4/2002 | Lin et al. |
| 6,383,519 B1 | 5/2002 | Sapieszko et al. |
| 6,409,972 B1 | 6/2002 | Chan |
| 6,485,754 B1 | 11/2002 | Wenz et al. |
| 6,491,900 B2 | 12/2002 | Chow et al. |
| 6,511,510 B1 | 1/2003 | de Bruijn et al. |
| 6,521,246 B2 | 2/2003 | Sapieszko et al. |
| 6,547,866 B1 | 4/2003 | Edwards et al. |
| 6,558,709 B2 | 5/2003 | Higham |
| 6,585,992 B2 | 7/2003 | Pugh et al. |
| 6,616,742 B2 | 9/2003 | Lin et al. |
| 6,642,285 B1 | 11/2003 | Bohner |
| 6,648,960 B1 | 11/2003 | Lin et al. |
| 6,670,293 B2 | 12/2003 | Edwards et al. |
| 6,706,690 B2 | 3/2004 | Reich et al. |
| 6,713,420 B2 | 3/2004 | Imura et al. |
| 6,719,993 B2 | 4/2004 | Constantz |
| 6,733,582 B1 | 5/2004 | Bohner et al. |
| 6,793,725 B2 | 9/2004 | Chow et al. |
| 6,800,360 B2 | 10/2004 | Miyanaga et al. |
| 6,821,916 B2 | 11/2004 | Myoi et al. |
| 6,887,488 B2 | 5/2005 | Cui et al. |
| 6,929,692 B2 | 8/2005 | Tas |
| 6,979,700 B2 | 12/2005 | Ma |
| 6,994,726 B2 | 2/2006 | Lin et al. |
| 7,070,722 B1 * | 7/2006 | Gilchrist ............ A61K 9/122 156/305 |
| 7,118,705 B2 | 10/2006 | Lin et al. |
| 7,151,120 B2 | 12/2006 | Ma |
| 7,163,651 B2 | 1/2007 | Chern Lin et al. |
| 7,189,263 B2 | 3/2007 | Erbe et al. |
| 7,258,734 B2 | 8/2007 | Lin et al. |
| 7,291,345 B2 | 11/2007 | Winterbottom et al. |
| 7,294,187 B2 | 11/2007 | Chow et al. |
| 7,318,841 B2 | 1/2008 | Tofighi et al. |
| 7,326,426 B2 | 2/2008 | Nathan et al. |
| 7,351,280 B2 | 4/2008 | Khairoun et al. |
| 7,407,542 B2 | 8/2008 | Lemaitre et al. |
| 7,416,602 B2 | 8/2008 | Murphy et al. |
| 7,459,018 B2 | 12/2008 | Insley et al. |
| 7,473,312 B2 | 1/2009 | Barralet et al. |
| 7,494,950 B2 * | 2/2009 | Armitage ............ A61K 31/74 106/35 |
| 7,531,004 B2 | 5/2009 | Bagga et al. |
| 7,534,451 B2 | 5/2009 | Erbe et al. |
| 7,709,029 B2 | 5/2010 | Chow et al. |
| 7,858,079 B2 | 12/2010 | Hadba et al. |
| 7,892,346 B2 | 2/2011 | Insley et al. |
| 7,892,347 B2 | 2/2011 | Insley et al. |
| 2002/0018797 A1 | 2/2002 | Cui et al. |
| 2002/0055143 A1 | 5/2002 | Bell et al. |
| 2002/0120351 A1 | 8/2002 | Tuomela et al. |
| 2002/0155167 A1 | 10/2002 | Lee et al. |
| 2003/0021824 A1 | 1/2003 | Lacout et al. |
| 2003/0049329 A1 | 3/2003 | Lee et al. |
| 2003/0078317 A1 | 4/2003 | Lin et al. |
| 2003/0152606 A1 | 8/2003 | Gerber |
| 2004/0048947 A1 | 3/2004 | Lidgren et al. |
| 2004/0064194 A1 | 4/2004 | Irie et al. |
| 2004/0137032 A1 | 7/2004 | Wang |
| 2004/0141903 A1 | 7/2004 | Zitelli et al. |
| 2004/0151751 A1 | 8/2004 | Cooper |
| 2004/0244651 A1 | 12/2004 | Lemaitre et al. |
| 2004/0258729 A1 | 12/2004 | Czernuszka et al. |
| 2004/0266943 A1 | 12/2004 | Oriakhi |
| 2005/0008672 A1 | 1/2005 | Winterbottom et al. |
| 2005/0029701 A1 | 2/2005 | Lin et al. |
| 2005/0074415 A1 | 4/2005 | Chow et al. |
| 2005/0087903 A1 | 4/2005 | Farr et al. |
| 2005/0119746 A1 | 6/2005 | Lidgren |
| 2005/0184417 A1 | 8/2005 | Chern Lin et al. |
| 2005/0199156 A1 | 9/2005 | Khairoun et al. |

(56) References Cited

U.S. PATENT DOCUMENTS

| | | |
|---|---|---|
| 2005/0230870 A1 | 10/2005 | Oriakhi |
| 2005/0267592 A1 | 12/2005 | Lin et al. |
| 2005/0271740 A1 | 12/2005 | Lin et al. |
| 2005/0271741 A1 | 12/2005 | Lin et al. |
| 2005/0271742 A1 | 12/2005 | Chern Lin et al. |
| 2006/0205652 A1 | 9/2006 | Zamora et al. |
| 2006/0225620 A1 | 10/2006 | Murphy et al. |
| 2006/0263443 A1 | 11/2006 | Chow et al. |
| 2007/0041906 A1 | 2/2007 | Lidgren et al. |
| 2007/0092580 A1 | 4/2007 | Chow et al. |
| 2007/0092856 A1 | 4/2007 | Chow et al. |
| 2007/0128245 A1 | 6/2007 | Rosenberg et al. |
| 2007/0186818 A1 | 8/2007 | Bohner |
| 2007/0189951 A1 | 8/2007 | Constantz et al. |
| 2007/0202075 A1 | 8/2007 | Hadba et al. |
| 2007/0218144 A1 | 9/2007 | Lally |
| 2007/0260325 A1 | 11/2007 | Wenz |
| 2007/0282455 A1 | 12/2007 | Luginbuehl et al. |
| 2007/0283849 A1 | 12/2007 | Edidin et al. |
| 2008/0014242 A1 | 1/2008 | Overby et al. |
| 2008/0153784 A1 | 6/2008 | Zhang et al. |
| 2008/0194810 A1 | 8/2008 | Kim et al. |
| 2008/0206716 A1 | 8/2008 | Asgary |
| 2008/0208354 A1 | 8/2008 | Bohner et al. |
| 2008/0305517 A1 | 12/2008 | Griffin et al. |
| 2009/0048145 A1 | 2/2009 | Hellerbrand et al. |
| 2009/0054545 A1 | 2/2009 | Muratoglu et al. |
| 2009/0158964 A1 | 6/2009 | Insley et al. |
| 2009/0280179 A1 | 11/2009 | Neumann et al. |
| 2011/0062046 A1 | 3/2011 | Hadba et al. |

FOREIGN PATENT DOCUMENTS

| | | | |
|---|---|---|---|
| CA | 2669777 A1 | 10/2006 | |
| CN | 1844010 A | 10/2006 | |
| CN | 101264338 A | 9/2008 | |
| EP | 0 627 899 | 12/1994 | |
| EP | 0 936 929 | 8/1999 | |
| EP | 1 237 585 | 9/2002 | |
| EP | 0 912 161 B1 | 2/2003 | |
| EP | 1 443 981 | 8/2004 | |
| EP | 1712245 A2 | 10/2006 | |
| EP | 1787626 A1 * | 5/2007 | ............. A61K 6/033 |
| EP | 1938844 A2 | 7/2008 | |
| EP | 2260877 A1 | 12/2010 | |
| JP | 2006130122 A | 5/2006 | |
| JP | 2006-289902 A | 10/2006 | |
| JP | 2006289092 A | 10/2006 | |
| JP | 05-023387 B1 | 9/2012 | |
| WO | 93/16657 | 9/1993 | |
| WO | 9416951 A1 | 8/1994 | |
| WO | 98/016268 A2 | 4/1998 | |
| WO | 00/007639 A1 | 2/2000 | |
| WO | 01/041824 A1 | 6/2001 | |
| WO | 04/000374 A1 | 12/2003 | |
| WO | 04/103419 | 12/2004 | |
| WO | 05/009481 | 2/2005 | |
| WO | 2005/084726 | 9/2005 | |
| WO | 2005117919 A2 | 12/2005 | |
| WO | 2007/090880 A2 | 8/2007 | |
| WO | 2008/014561 A1 | 2/2008 | |
| WO | 2010116321 A2 | 10/2010 | |

OTHER PUBLICATIONS

Barralet, Grover, Gbureck, 'Ionic Modification of Calcium Phosphate Cement Viscosity. Part II: Hypodermic Injection and Strength Improvement of Brushite Cement.', Biometerials, vol. 25, No. 11, pp. 2197-2203, May 2004.

Biotek, Inc.,"Hydroformed Microspheres as New Injectable Drug Vehicle", 1994.

Boyce et al., J. Biomedic. Mater. Res., vol. 26,547-553 (1992).

Burguera EF, Xu HH, Weir MD, Injectable and rapid-setting calcium phosphate bone cement with dicalcium phosphate dihydrate, J Biomed Mater res B Appl Biomater, Sep. 23, 2005.

Burguera, Guitian, Chow, "A water setting tetracalcium phosphate-dicalcium phosphate dihydrate cement", Wiley Periodicals, vol. 71A, No. 2, Oct. 2004.

Chow et al., AADR Abstract, No. 666, 1992.

Chow et al., IADR Abstract No. 2410, Apr. 1991.

Freche, M. & Heughebaert, J.C.; Calcium Phosphate Precipitation in the 60-80oC Range, Journal of Crsytal Growth, vol. 94 (1989), pp. 947-954.

Gbureck, Barralet, Spatz, Grover, Thull 'Ionic Modification of Calcium Phosphate Cement Viscosity. Part I: Hypodermic Injection and Strength Improvement of Apatite Cement.', Biometerials, vol. 25, No. 11, pp. 2187-2195, May 2004.

Gbureck, Dembski, Thull, Barralet, "Factors influencing calcium phosphate cement shelf-life", Biomaterials, May 26, 2004.

Ginebra et al. Biomaterials 25:3453-3462 (2004).

Gisep, Kugler, Wahl, Rahn, 'Mechanical Characterization of a Bone Defect Model Filled with Ceramic Cements', J Mater Sci Mater Med, vol. 15, No. 10, pp. 1065-1071, Oct. 2004.

International Search Report, PCT/US2010/060793, dated Apr. 18, 2011.

Japanese Office Action for Application No. 2012-508835 dated Apr. 20, 2012.

Jensen, Ooms, Verdonschot, Wolke, 'Injectable Calcium Phosphate Cement for Bone Repair and Implant Fixation', Orthop Clin North Am, vol. 36, No. 1, pp. 89-95, Jan. 2005.

Komath, Varma , "Development of a fully injectable calcium phosphate cement for Orthopedic and Dental Applications", Bull. Matter. Sci, Jun. 2003, pp. 415-422.

Komath, Varma and Sivakumar, "On the development of an apatitic calcium phosphate bone cement", Bull. Matter. Sci, vol. 23, No. 2, Apr. 2000, pp. 135-140.

Lee at al., "A Critical Role for the Membrane-type-1 Matrix Metalloproteinase in Collagen Phagocytosis." 2006, Mol Bioi Cell17: 4812-4826.

MacPhee et al., Curr. Opin. Solid State Mater Sci., vol. 8, 141-149 (2004).

Moreau et al., J. Biomed. Mater. Res. A., 91(2): 605-613 (2009).

Murphy, Clarkin & Insley,'Calcium Phosphate Bone Cements of the Future: Towards the Understanding of their Chemistry', Biomaterials Research Group, Sep. 2005.

nerac.com, "Injectable Calcium Phosphate Cement" Retro Search, p. 1-151, Printed Oct. 14, 2005.

Rocha et al., Biomaterials, vol. 23, 449-456 (2002).

Salem et al., Adv. Mater., vol. 15., No. 3, 210-213 (2003).

Segman-Magidovich et al., Adv. Mater., vol. 20, 2156-2161 (2008).

Tofighi A, Mounic S, Chakaravarthy P, Rey C, Lee D, "Setting Reactions Involved in Injectable Cements Based on Amorphous Calcium Phosphate", Key Engineering Materials, vol. 192-195, pp. 769-772, 2001.

Wach et al. (nuclear instruments and Methods in Physics Research B 2003 211, 533-544.

Zhang et al., Semin. Cancer Bioi., vol. 15,413-420 (2005).

International Search Report and Written Opinion for PCT/EP2010/067196 dated Oct. 14, 2011.

\* cited by examiner

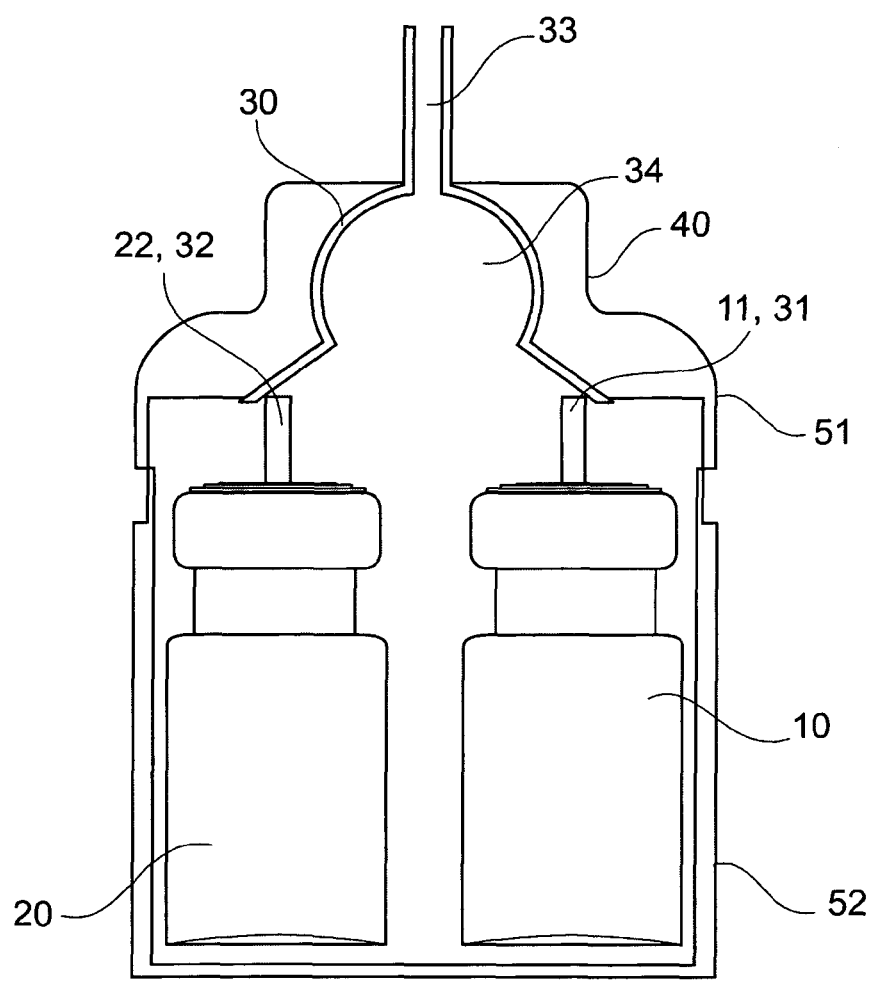

POLYMERIC BONE FOAM COMPOSITION AND METHOD

CROSS-REFERENCE TO RELATED APPLICATION

The present application is a national phase entry under 35 U.S.C. § 371 of International Application No. PCT/EP2010/067196 filed Nov. 10, 2010, published in English, incorporated herein by reference.

FIELD OF THE INVENTION

The present invention is related to new biomaterials, in particular bone foams, a process for preparing such materials as well as an applicator for applying the biomaterials directly to the patient's application site. Further, the present invention is directed to the use of a composition comprising water, a surfactant and a propellant in the preparation of a bone foam.

BACKGROUND OF THE INVENTION

The natural capability of the human body to regenerate bone defects is not sufficient. Therefore, for the human body is typically not possible to restore a fracture on its own. Medical implants are useful in providing sufficient stability for the fracture and support the curing process.

In cases where the bone damage is too severe, bone cements may also be applied to stabilize implants and thereby support the curing of the defect.

Bone cements may act as an artificial "linker" between the natural bone and the implant. Usually, bone cements are classified into two general classes, so called PMMA bone cements (Poly Methyl Methacrylates) and calcium phosphate based cements.

Since the discovery of the calcium phosphate based cements in the mid 1980ies, various formulations have been developed. The underlying principle of these materials is that a mixture of one or more calcium salts with water or an aqueous solution forms a cement which due to a dissolution and precipitation process sets. The setting typically takes place under physiological conditions. The final reaction product (after setting) is typically a hydroxyapatite that is very similar to the biological material in terms of crystallinity and non-stoichiometry.

One of the main advantages of the calcium phosphate foams is their excellent biocompatibility and bioactivity. Moreover, the foam is capable of adapting to the geometry of the defect.

The properties of the resulting calcium phosphate foam (bone foam) can be adjusted by modifying various parameters such as the chemical composition of the starting material, the relative proportion of the constituents, additives (such as seeds, accelerants, retardants, etc.), particle size, pH value, liquid to powder ratio, temperature, humidity or the like.

The porosity of the bone foam is a further important parameter and is also important for the durability of e.g. implants. On the one hand, a high porosity is desired to allow for space for newly formed bone tissue. On the other hand, the higher the porosity of the resulting material, the smaller is its breaking strength.

Moreover, the handling of the current products is far from ideal. The application of bone cements into a void for example of an osteoporotic bone is very difficult as the cement paste is made outside the application site and subsequently applied into the damaged bone. Therefore, it is very difficult to apply the foam into small cavities which cannot be reached by the instrument with which the paste is applied to the damaged bone.

EP 1 787 626 describes an injectable self setting calcium phosphate foam for use as biomaterial. The foam is prepared by agitation and mechanical whipping and may subsequently be applied.

Particles for incorporation of particulate components in a calcium phosphate cement are for example known from U.S. Pat. No. 5,525,148 issued to Chow et al., U.S. Pat. No. 5,820,632 issued to Constantz et al., or JP 5,023,387 issued to Hirano et al.

One of the problems associated with the calcium phosphate bone foams of the prior art is that they are prepared extra corporally and only after preparation applied to the corresponding site of application in the body by manually controlled means, e.g. a syringe. For small application sites or complex geometric forms there is a need for an improved application of the foams and/or foams which are instantly applied to the application site after preparation ("direct to patient application").

SUMMARY OF THE INVENTION

It would be desirable to provide an improved calcium phosphate foam, process for the preparation of a calcium phosphate foam, use of a composition, solid state structure, calcium phosphate cement foam and bone foam applicator.

The invention provides calcium phosphate foam, process for the preparation of a calcium phosphate foam, use of a composition, solid state structure, and calcium phosphate cement foam and a bone foam applicator according to the subject matter of the independent claims. Further embodiments are incorporated in the dependent claims.

According to an exemplary embodiment of the invention, there is provided a process for the preparation of a calcium phosphate foam wherein the foam is obtainable by the mixture of at least two phases, a first phase comprising water and a second phase comprising one or more sources for calcium and/or phosphate, and wherein the foaming is performed during the mixture of the at least two phases. The first and/or the second phase may optionally further comprise a propellant. The term "during the mixture" of the at least two phases should be understood that the foaming of the cement starts just before, immediately when or substantially immediately when the first and the second phases are being contacted.

Thus, the process may provide a bone foam which is foamed in situ while mixing the first and the second phase so that no sequential foaming of the mixed cement paste or any precursors thereof is required any more. The optional propellant may be used for foaming the respective first and second phase.

According to another exemplary embodiment of the invention, the use of a composition comprising water, a surfactant and a propellant in the preparation of a calcium phosphate foam is provided, wherein the composition is contacted with at least one phase comprising one or more sources for calcium and/or phosphate.

Thus, the use of the composition allows for an in-situ foaming of the cement paste which is obtained upon mixing of the composition comprising water and the one or more sources for calcium and/or phosphate by the propellant, so that no additional step of foaming of the cement paste is required.

According to another exemplary embodiment of the invention the calcium phosphate foam obtainable by the above described process for use in bone regeneration, tissue engineering or as a bone substitute is provided.

According to an exemplary embodiment of the invention the solid state structure obtainable by the above described process after setting of the foam is provided. A solid state structure for use in bone surgery, bone regeneration, bone defect fillings, stabilization of bone fractures, fixing of implants, tissue engineering or as a bone substitute is also provided.

According to an exemplary embodiment of the invention there is provided a bone foam applicator, comprising a first container for storing a first composition having a first outlet, a second container for storing a second composition having a second outlet, a mixing arrangement having a first inlet and a second inlet, and an application outlet, an activation unit, wherein the first outlet is connected to the first inlet, and the second outlet is connected to the second inlet, wherein the activation unit is adapted to activate a convey of the first composition from the first container and the second composition from the second container to the mixing arrangement, wherein the mixing arrangement comprises a mixing volume being connected to the first inlet, the second inlet and the application outlet, wherein the mixing volume being adapted for mixing the first composition and the second composition within the mixing volume for foaming the mixed first composition and second composition when exiting the application outlet.

Thus, a bone foam applicator may be provided by which the first composition and the second composition may be mixed within the mixing volume before exiting the bone foam applicator. This allows a sufficient and reliable mixing process, in particular for medical compositions, like for example bone foam cement. In a medical application a reliable mixing process is of utmost importance, as for example bone foam cement is used during larger surgeries requiring save and reproducible processes. As a rule, the mixing process does not require further items or tools, as the mixing takes place within the bone foam applicator, i.e. within a mixing volume. This further allows providing the bone foam applicator as a simple single or multiple use device, which the surgeon may take from a storage when required during the surgery. In addition the first and second composition may be compositions which are activated when being mixed, so that this activation may take place on demand when applying the bone foam to the application site. Before activation, the compositions may be stored, without being activated. It should be noted that also more than two composition may be used, which as a rule requires more than two containers.

According to an exemplary embodiment of the invention at least one of the first container and the second container are adapted to store a propellant for blowing out the respective first and second compositions.

Thus, no further drive is required for conveying the mixture of the first and second composition. The bone foam applicator may be designed such that only a low force application is required for activation.

According to an exemplary embodiment of the invention the activation unit is integrally formed with the mixing arrangement and adapted to activate at least one valve positioned in the respective first and second outlet of the respective first and second container.

Thus, the number of movable parts may be reduced. A reduced number of movable parts as a rule lead to a higher reliability of the entire device.

According to an exemplary embodiment of the invention, the first container comprises water and optionally a propellant, and the second container comprises one or more sources for calcium and/or phosphate.

Thus, the bone foam may be obtained in situ by activation the bone foam applicator. The water from the first container and the sources for calcium and/or phosphate from the second container each enter the mixing volume. Within the mixing volume the bone foam will be generated in-situ. The generated bone foam may exit the mixing volume via the application outlet so that the bone foam may be directly applied to the patient's application site, when directing the application outlet directly to the patient's site. The application outlet may be provided with an extension like a tube or a conduit for an easier application. The tip of the application exit or the extension may be provided with an application head. The application head may have a plurality of openings and/or nozzles each pointing into different directions. The finalization of the chemical process of foam generation may also take place at the patient's site, i.e. at least a part of the chemical reaction, the final expansion and/or the hardening of the bone foam.

It should be noted that the above features may also be combined. The combination of the above features may also lead to synergetic effects, even if not explicitly described in detail.

These and other aspects of the present invention will become apparent from and elucidated with reference to the embodiments described hereinafter.

BRIEF DESCRIPTION OF THE DRAWINGS

Exemplary embodiments of the present invention will be described in the following, at least a part of it with reference to the following drawings.

FIG. 1 illustrates a bone foam applicator in parts with a front output orifice according to an embodiment of the invention.

DETAILED DESCRIPTION OF EXEMPLARY EMBODIMENTS

According to an exemplary embodiment of the invention, there is provided a process for the preparation of a calcium phosphate foam wherein the foam is obtainable by the mixture of at least two phases, a first phase comprising water and a second phase comprising one or more sources for calcium and/or phosphate, and wherein the foaming is performed during the mixture of the at least two phases. The first phase may optionally further comprise a propellant. The second phase may also optionally further comprise a propellant.

In one preferred embodiment of the invention, the first phase further comprises a propellant which allows for the foaming of the first and the second phase when the at least two phases are mixed. Upon mixing of the at least two phases, the cement paste is formed by the reaction of the first phase comprising water and the second phase comprising one or more sources of calcium and/or phosphate. The in-situ foaming of the cement paste formed from the at least two phases allows for the omission of an additional foaming step (e.g. performed by mechanical agitation) required by cement pastes described in the art.

In another exemplary embodiment of the invention, the first phase further comprises a stabilizing agent. The stabilizing agent supports the bubbles formed during foaming and thereby allow for a preparation of solid state structures exhibiting a higher macroporosity. A high macroporosity of the resulting solid state structure is desirable for bone regeneration and further conditions of interest of the present invention since it facilitates angiogenesis.

The stabilizing agent is preferably biocompatible.

The stabilizing agent is preferably selected from the group consisting of a surfactant, gelling agents, soluble phosphate salts, organic acids, and any mixtures thereof and more preferably is a surfactant.

The surfactant may be selected from the group consisting of a cationic, anionic or non-ionic surfactant and is preferably a non-ionic surfactant. In an alternative preferred embodiment of the present invention, the surfactant is a polymeric surfactant.

The surfactant that may be applied in the present invention are selected from the group consisting of substituted polyethylenglycols, PEGylated fatty acid derivatives, PEGylated glycerol fatty acid derivatives, PEGylated sorbitan fatty acid derivatives, and polypropylene glycol-PEG-blockpolymers derivatives and is preferably selected from the group consisting of PEG-glycerol rizinoleate, PEG-gycerol-hydroxystearate, polypropylene glycol-PEG-block-polymer, PEG-hydroxystearate, and PEG-sorbitan-monooleate. In particular, PEG-35-glycerol rizinoleates, PEG-40-gycerol-hydroxystearates, PEG-15-hydroxystearates, PEG-20-sorbitan-monooleates are preferred. Suitable surfactants that may be applied in the present invention are for example Cremophor EL®, Cremophor RH400®, Poloxamer 188®, Solutol HS 15®, or Tween 80®.

In case a stabilizing agent is present in the first composition, the stabilizing agent is present between 0.1% and 10% by weight, 0.5% to 7.5% or 0.5% to 3% based on the first phase. In a preferred embodiment, wherein the stabilizing agent is a surfactant, the surfactant is present between 0.1% and 10% by weight, 0.5% to 7.5% or 0.5% to 3% based on the first phase.

In an exemplary embodiment of the invention, the first phase further comprises a propellant. The propellant may be selected from the group consisting of propane, butane, iso-butane, heptafluoropropane, pentafluorobutane, and tetrafluoroethane and any mixtures of the foregoing. In a preferred embodiment, the propellant may be present between 5% and 25% by weight/weight based on the first phase.

The properties of foam may also be adjusted by the vapor pressure of the propellant in the first phase. In a preferred embodiment of the invention, the vapor pressure of the propellant is from about 1.1 to about 8 bar, preferably from about 1.3 to about 6 bar, and more preferably from about 1.5 to about 5 bar.

The compositions of the present invention may further comprise components selected from the group consisting of binders, accelerators, cohesion promoters, and any mixtures of the foregoing.

Binders suitable for use in the present invention are selected from the group consisting of sodium alginate, hydroxypropyl methyl cellulose, hydroxyethyl cellulose, hydroxypropyl cellulose, methyl cellulose, hydroxyethyl starch, soluable starch, cyclodextrin, dextran sulphate, polyvinylpyrrolidone, chitosan, hyaluronic acid and any mixtures of the foregoing. The binders are preferably present in the range from 0.1% to 10% by weight, more preferably from 0.5% to 5% by weight based on the first phase. Polyvinylpyrrolidone is preferred.

Accelerators of the setting reaction may be selected from the group consisting of $Na_2HPO_4$, $NaH_2PO_4$, tri-sodiumcitrate-dihydrate, $KH_2PO_4$, or $K_2HPO_4$ or any mixtures thereof. Preferably, the accelerator is present in the range from 0.1 to 10% (by weight), preferably in the range from 0.5% to 5% based on the first composition.

The reagents of the second phase of the cement include a source of calcium and a source of phosphate, which can be present as a single component or as two or more components. In case of a single source both calcium and phosphate are comprised therein. In case two or more components are applied as the source for calcium and/or phosphate, either each of them comprises calcium and phosphate or the sources for calcium and phosphate are present in separate components. The second phase comprises a calcium and/or a phosphate source selected from the group consisting of a) at least a source of calcium and/or phosphate selected from tetracalcium phosphate, dicalcium phosphate anhydride, dicalcium phosphate dihydrate, alpha tricalcium phosphate, beta tricalcium phosphate, monocalcium phosphate monohydrate, hydroxyapatite, calcium deficient hydroxyapatite, fluorapatite, amorphous calcium phosphate, calcium-sodium- and potassium-phosphate, calcium- and sodium-phosphate, calcium- and potassium-phosphate, and calcium pyrophosphate; or alternatively, b) at least a compound of calcium selected from calcium carbonate, calcium sulphate, calcium sulphate hemi hydrate, calcium oxide, and calcium hydroxide, and at least a compound of phosphate selected from phosphoric acid and all the soluble phosphates; or alternatively c) a mixture of at least a compound defined in option a) and at least a compound defined in option b).

From these sources of calcium and/or phosphate tetracalcium phosphate, dicalcium phosphate anhydride, dicalcium phosphate dihydrate, alpha tricalcium phosphate, beta tricalcium phosphate, monocalcium phosphate monohydrate, hydroxyapatite, calcium deficient hydroxyapatite, fluorapatite, amorphous calcium phosphate, calcium-sodium- and potassium-phosphate, calcium- and sodium-phosphate, calcium- and potassium-phosphate, and calcium pyrophosphate are preferred.

Even more preferably, the second phase comprises tetracalcium phosphate, di-calciumphosphate or mixtures thereof, and preferably the ratio of tetra-calcium phosphate to di-calciumphosphate is between 1:5 and 5:1 and more preferably between 1:3 and 3:1. A suitable source for calcium and/or phosphate is e.g. the mixture of dicalcium phosphate dihydrate, tetracalcium phosphate comprising trisodium citrate sold under the tradename "HydroSet®" by Stryker®.

In a further preferred embodiment of the invention, the particle size of the calcium and/or phosphate source is in the range of 0.05 to 100 µm, and preferably is between 0.1 and 75 µm, more preferably is between 0.2 and 50 µm, and even more preferably between 0.5 and 10 µm.

The particle size distribution is determined by methods known to the person skilled in the art such as laser diffraction or photon correlation spectroscopy. In general, laser diffraction is used when determining particle size distribution of particles about 0.5 µm or larger. For example suitable apparatus such as a laser diffractometer "Helos" of the company Sympatec may be used. Photon correlation spectroscopy is applied for particle size distribution of 5 µm or less. A suitable apparatus for Photon correlation spectroscopy is the Malvern Zetasizer Nano-ZS. Particle size distributions between 0.5 µam and 5 µm may be analyzed by either of the two methods described above.

In a further exemplary embodiment of the invention, the second phase may preferably comprise a further component selected from the group consisting of an alcohol, a propellant, and any mixtures thereof.

The foam prepared by the process of the present invention may comprise an active agent (such as anticancer agents, antibiotics and/or antioxidants), a viable cell, or a growth factor or a combination of the foregoing. Preferably, these additional components are added in form of a solution or suspension. The use of an osteoblast suspension is preferred.

The process of the present invention allows for an in situ preparation of the bone foam. Thus, the foaming starts immediately when the first and the second phase are mixed. After formation of the foam it sets in less than 60 min, less than 50 min, less than 40 min, less than 30 min, less than 15 min, less than 10 min, less than 8 min, or less than 5 min at 37° C.

In an exemplary embodiment of the present invention, the ratio of the first phase and the second phase is between 10:1 and 1:10, and preferably between 8:1 and 1:8, and even more preferably 5:1 and 1:5.

The calcium phosphate foam according to the present invention comprises calcium phosphate cement and at least one stabilizing agent.

The stabilizing agent is preferably selected from the group consisting of a surfactant, gelling agents, soluble phosphate salts, organic acids, and any mixtures thereof and more preferably is a surfactant.

Suitable soluble phosphate salts are preferably selected from the group consisting of primary phosphates (dihydrogen phosphates), secondary phosphates (hydrogen phosphates) and tertiary phosphates, preferably alkaline or alkaline earth phosphates such as $NaH_2PO_4$, $KH_2PO_4$, $Na_2HPO_4$, $K_2HPO_4$, $Na_3PO_4$, or $K_3PO_4$.

Suitable organic acids are preferably selected from the group consisting of organic acid selected from oxalic acid, acetic acid, formic acid, malic acid, maleic acid, malonic acid, succinic acid, fumaric acid, phthalic acid, terephthalic acid, citric acid, tartaric acid, methanesulfonic acid, ethanesulfonic acid, p-toluenesulfonic acid, trifluoroacetic acid, ascorbic acid, fatty acids and the like. Citric acid is preferred.

The surfactant may be selected from the group consisting of a cationic, anionic or non-ionic surfactant and is preferably a non-ionic surfactant. In an alternative preferred embodiment of the present invention, the surfactant is a polymeric surfactant. With respect to the preferred surfactants, it is referred to the above mentioned preferred surfactants.

The calcium phosphate foam according to the present invention has preferably a viscosity which allows for a direct application of the calcium phosphate foam to the application site e.g. with the applicator of the present invention described above. The calcium phosphate foam is capable of being applied to and fill small cavities before setting. The viscosity of the calcium phosphate foam of the present invention (non hardened) is between 100 and 100.000 cP at 20° C.

Calcium phosphate foam of the present invention exhibits (after setting) a macroporosity in the range of 5 to 90 vol.-%, preferably in the range of 15 to 80 vol.-%, more preferably between 20 and 80%, even more preferably between 25 and 80 vol.-% and more preferably 30 and 80%, and most preferably between 35 and 80%. Said set foam (a solid state structure) comprises pores having a diameter comprising between 10 and 1000 μm, preferably between 100 and 800 μm. The size of the pores may be adjusted by various parameters such as the concentration of the stabilizing agent or the particle size of the calcium and/or phosphate sources.

Preferably the macropores are interconnected. Interconnectivity of the pores may be induced by the foaming process. However, the interconnectivity of the pores may be increased by measures known to the skilled person such as incorporation of particulate components in the second phase. These particulate components should be insoluble in the cement but dissolve after being exposed to physiological conditions after the cement foam has set. Such particles are for example mentioned in U.S. Pat. No. 5,525,148 issued to Chow et al., U.S. Pat. No. 5,820,632 issued to Constantz et al., or JP 5,023,387 issued to Hirano et al., all incorporated herein by reference.

Preferably the calcium phosphate foam of the present invention exhibits a setting time measured by the Gillmore needles method less than 45 min, less than 35 min, less than 25 min, less than 15 min, less than 10 min, less than 8 min, or less than 5 min. Alternatively, a Zwick/Roell Materialprüfer Z2.5 may also be applied for determination of the setting time.

In a further exemplary embodiment, the calcium phosphate foam preferably is stable for at least 15 min, at least 30 min, at least 40 min, at least 45 min, at least 50 min, or at least 60 min. The stability of the foam is measured by the so called "cylinder method", in which a measuring cylinder is filled with foam and by determination of the respective foam and liquid volume at specific time points, the stability of the foam is determined. If the stability of the foam is sufficient, the foam sets in the foamed structure to form a corresponding solid state structure.

In a further exemplary embodiment of the invention, the calcium phosphate foam is self setting, preferably under physiological conditions (e.g. temperature, aqueous environment).

In yet another exemplary embodiment of the invention, the foam further preferably comprises a crosslinking agent. The crosslinking agent assists in the setting of the foam.

A further aspect of the present invention is directed to a use of a composition comprising water, a surfactant and a propellant in the preparation of a calcium phosphate foam comprising contacting said composition with at least one phase comprising one or more sources for calcium and/or phosphate. The use of the composition comprising water, a surfactant and a propellant allows for an in-situ foaming of the cement paste, once the composition has been brought in contact with one or more sources for calcium and/or phosphate. Thereby no additional foaming step of either the first or the second phase or the cement paste is required any more.

Suitable surfactant and propellants for the use have been described above.

The solid state structure and the calcium phosphate foam of the present invention may be used in bone surgery, bone regeneration, bone defects filling, stabilization of bone fractures, fixing of prostheses or implants, and tissue engineering scaffolds.

FIG. 1 illustrates a bone foam applicator with a front output orifice according to an embodiment of the invention. The bone foam applicator comprises a first container 10 for storing a first composition and a second container 20 for storing a second composition. Both containers each have an outlet 11, 22. The applicator further comprises a mixing arrangement 30 having a first inlet 31 and a second inlet 32, and an application outlet 33. The first outlet is connected to the first inlet, and the second outlet is connected to the second inlet. The mixing arrangement serves for mixing the first and second composition. The mixing process may be activated by an activation unit 40. The activation unit is adapted to activate a conveyance of the first composition from the first container and the second composition from the second container to the mixing arrangement. The mixing arrangement comprises a mixing volume 34 being connected to the first inlet, the second inlet and the application outlet, wherein the mixing volume is adapted for mixing the first composition and the second composition within the mixing volume for foaming the mixed first composition and second composition when exiting the application outlet. The containers 10, 20 may be stored in a first housing part. The mixing arrangement 30 may movably located to the first housing part 51, such that a second housing part 52 may cover the containers 10, 20 and the mixing arrangement 30. An activating element 40 in form of a push button may serve as a lever to push down the entire mixing arrangement 30 to set free the both compositions from the respective container 10, 20.

In all described devices the first container may comprise water and optionally a propellant, and the second container may comprise one or more sources for calcium and/or phosphate. Thus, the bone foam may be obtained in situ by activation the bone foam applicator. The water from the first container and the sources for calcium and/or phosphate from the second container each may enter the mixing volume. Within the mixing volume the bone foam will be generated in-situ. The generated bone foam may exit the mixing volume via the application outlet so that the bone foam may be directly applied to the patient's application site, when directing the application outlet directly to the patient's site. The application outlet may be provided with an extension like a tube or a conduit for an easier application (not shown). The tip of the application exit or the extension may be provided with an application head (not shown). The application head may have a plurality of openings and/or nozzles each pointing into different directions. This allows a better distribution of the applied foam. The finalization of the chemical process of foam generation may also take place at the patient's site, i.e. at least a part of the chemical reaction, the final expansion and/or the hardening of the bone foam.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features. It has to be noted that exemplary embodiments of the invention are described with reference to different subject matters. In particular, some exemplary embodiments are described with reference to apparatus type claims whereas other exemplary embodiments are described with reference to method type claims. However, a person skilled in the art will gather from the above and the following description that, unless other notified, in addition to any combination of features belonging to one type of subject matter also any combination, in particular between features relating to different subject matters, in particular between features of the apparatus type claims and features of the method type claims is considered to be disclosed with this application.

In the claims, the word "comprising" does not exclude other elements or steps, and the indefinite article "a" or "an" does not exclude a plurality. The mere fact that certain measures are re-cited in mutually different dependent claims does not indicate that a combination of these measures cannot be used to advantage.

REFERENCE LIST 10 first container
11 first outlet
20 second container
22 second outlet
30 mixing arrangement
31 first inlet
32 second inlet
33 application outlet
34 mixing volume
40 activation unit
51 first housing part
52 second housing part

The invention claimed is:

1. A process for preparing a calcium phosphate bone foam comprising:
   mixing a) a first phase comprising water, a propellant in the amount of 5% to 25% by weight of the first phase, and a stabilizing agent in the amount of 0.1% to 10% by weight of the first phase, and
   b) a second phase comprising a calcium and/or phosphate source, and initiating foaming during the mixing of the first and second phases,
   wherein the calcium and/or phosphate source is selected from the group consisting of:
   a) a calcium/phosphate compound is selected from the group consisting of: tetracalcium phosphate, dicalcium phosphate anhydride, dicalcium phosphate dihydrate, alpha tricalcium phosphate, beta tricalcium phosphate, monocalcium phosphate monohydrate, hydroxyapatite, calcium deficient hydroxyapatite, fluorapatite, amorphous calcium phosphate, calcium-sodium- and potassium-phosphate, calcium- and sodium-phosphate, calcium- and potassium-phosphate, and calcium pyrophosphate;
   b) a composition comprising a calcium compound and a phosphate compound, wherein
      i. the calcium compound is selected from the group consisting of calcium carbonate, calcium sulphate, calcium sulphate hemi hydrate, calcium oxide, and calcium hydroxide; and
      ii. the phosphate compound selected from the group consisting of: phosphoric acid, primary phosphates, dihydrogen phosphates, secondary phosphates, hydrogen phosphates, tertiary phosphates, alkaline phosphates, alkaline earth phosphates, $NaH_2PO_4$, $KH_2PO_4$, $Na_2HPO_4$, $K_2HPO_4$, $Na_3PO_4$, and $K_3PO_4$; and
   c) a mixture of at least the calcium/phosphate compound defined in option a) and at least the composition defined in option b),
   wherein the foaming is performed during mixing of the two phases and wherein the calcium phosphate bone foam has a viscosity between 100 and 100,000 cP at 20° C.

2. The process of claim 1, wherein the stabilizing agent is selected from the group consisting of a surfactant, gelling agent, primary phosphates, dihydrogen phosphates, secondary phosphates, hydrogen phosphates, tertiary phosphates, alkaline phosphates, alkaline earth phosphates, $NaH_2PO_4$, $KH_2PO_4$, $Na_2HPO_4$, $K_2HPO_4$, $Na_3PO_4$, $K_3PO_4$, organic acids, and combinations thereof.

3. The process of claim 2, wherein the surfactant is at least one of
(i) a cationic, anionic or non-ionic surfactant;
(ii) a polymeric surfactant; or
(ii) PEGylated fatty acid derivatives, PEGylated glycerol fatty acid derivatives, PEGylated sorbitan fatty acid, and polypropylene glycol-PEG-blockpolymer derivatives and preferably is selected from the group consisting of PEG-35-glycerol rizinoleate, PEG-40-gycerol-hydro xystearate, polypropylene glycol-PEG-blockpolymer, PEG-15-hydroxystearate, or PEG-20-sorbitan-monooleate.

4. The process of claim 1, wherein the propellant in the first phase is selected from the group consisting of propane, butane, iso-butane, heptafluoropropane, pentafluorobutane, and tetrafluoroethane and any mixtures thereof.

5. The process of claim 1, wherein the first phase is formulated with a vapor pressure of the propellant of about 1.1 to about 8 bar.

6. The process of claim 1, wherein the first phase further comprises at least one component selected from the group consisting of binders, accelerators, cohesion promoters, and any mixtures thereof, wherein the binder is polyvinylpyrrolidone and the accelerator is selected from the group consisting of: $Na_2HPO_4$, $NaH_2PO_4$, tri-sodiumcitrate dihydrate, $KH_2PO_4$, or $K_2HPO_4$ and combinations thereof; and
the second phase further comprises a component selected from the group consisting of: an alcohol, a propellant, and combinations thereof.

7. The process according to claim 1, wherein the particle size of the calcium and/or phosphate source is in the range of 0.05 to 100 μm.

8. The process of claim 1, wherein the second phase comprises tetra-calcium phosphate, di-calcium phosphate or mixture thereof, wherein the ratio of tetra-calcium phosphate to di-calciumphosphate is between 1:5 and 5:1.

9. The process of claim 1, wherein the foam further comprises an anticancer agent, an antibiotic, an antioxidant, a viable cell, a growth factor or a combination thereof.

10. The process of claim 1, wherein the foam sets in less than 60 min at 37° C., and the ratio of the first phase to the second phase is between 10:1 and 1:10.

* * * * *